(12) United States Patent
Rangaswamy (10) Patent No.: US 11,613,512 B2
(45) Date of Patent: Mar. 28, 2023

(54) PRODUCTION OF MALIC ACID

(71) Applicant: THIRUMALAI CHEMICALS LIMITED, Mumbai (IN)

(72) Inventor: Parthasarathy Rangaswamy, Vellore (IN)

(73) Assignee: THIRUMALAI CHEMICALS LIMITED, Mumbai (IN)

(*) Notice: Subject to any disclaimer, the term of this patent is extended or adjusted under 35 U.S.C. 154(b) by 0 days.

(21) Appl. No.: 17/452,735

(22) Filed: Oct. 28, 2021

(65) Prior Publication Data
US 2022/0048845 A1 Feb. 17, 2022

Related U.S. Application Data

(63) Continuation of application No. PCT/IN2020/050608, filed on Jul. 15, 2020.

(30) Foreign Application Priority Data

Jul. 16, 2019 (IN) .............................. 201921028680
Mar. 5, 2020 (IN) .............................. 202021009475

(51) Int. Cl.
C07C 51/087 (2006.01)
C07C 51/367 (2006.01)

(52) U.S. Cl.
CPC .......... *C07C 51/087* (2013.01); *C07C 51/367* (2013.01)

(58) Field of Classification Search
None
See application file for complete search history.

(56) References Cited

U.S. PATENT DOCUMENTS 1,900,649 A * 3/1933 Alphons ................. C07C 51/43
562/593
3,141,037 A 7/1964 Olenberg et al.
(Continued)

FOREIGN PATENT DOCUMENTS

CN 1560016 A 1/2005
CN 103193739 A 7/2013
(Continued)

OTHER PUBLICATIONS

Lorz ("Phthalic Acid and Derivatives" Ullmann's Encyclopedia of Industrial Chemistry, 2012, p. 131-180) (Year: 2012).*
(Continued)

*Primary Examiner* — Amy C Bonaparte
(74) *Attorney, Agent, or Firm* — Knobbe, Martens, Olson & Bear, LLP (57) ABSTRACT

A method of production of malic acid includes treating a first intermediate product to form a second intermediate product. The treating includes substantially removing impurities from the first intermediate product to obtain a treated intermediate product by gas stripping the crude maleic anhydride, or subjecting a mixture of one or more of the crude maleic acid, the crude fumaric acid, and the vent gas scrubber solution obtained from a phthalic anhydride production process or a maleic anhydride production process to crystallization, passing an aqueous solution of the treated intermediate product through a carbon column to substantially remove retained impurities to form the second intermediate product, obtaining a feed that includes the second intermediate product, and causing the feed to undergo hydration reaction in a tubular reactor or a continuous stirred tank reactor to produce malic acid.

18 Claims, 5 Drawing Sheets

(56) References Cited

U.S. PATENT DOCUMENTS

| | | | |
|---|---|---|---|
| 3,379,756 A | 4/1968 | Ahlgren | |
| 3,379,757 A | 4/1968 | Winstrom et al. | |
| 3,523,024 A | 8/1970 | Nesty | |
| 4,035,419 A | 7/1977 | Sumikawa et al. | |
| 5,210,295 A | 5/1993 | Ramsey et al. | |

FOREIGN PATENT DOCUMENTS

| | | | |
|---|---|---|---|
| EP | 0515345 A2 | | 11/1992 |
| IN | 201621024815 | * | 8/2016 |
| IN | 201621024815 A | | 8/2016 |
| SU | 208706 A1 | | 1/1968 |
| SU | 218874 A1 | | 5/1968 |
| WO | 2012081043 A1 | | 6/2012 |

OTHER PUBLICATIONS

Lohbeck ("Maleic and Fumaric Acids" Ullmann's Encyclopedia of Industrial Chemistry, 2012, p. 146-155) (Year: 2012).*

Sauer ("Tubular Plug Flow Reactors" Ullmann's Encyclopedia of Industrial Chemistry, 2013, p. 1-23) (Year: 2013).*

Bzhasso ("New Catalysts for Maleic acid Hydration", Zhurnal Prikladnoi Khimii (Sankt-Peterburg, Russian Federation), 1969, 42(7), p. 1610-1614) (Year: 1969).*

Aluminum Chloride (hereafter referred to as "reference C", MSDS, downloaded from https://www.sigmaaldrich.com/US/en/sds/aldrich/563919 on Mar. 23, 2022) (Year: 2022).*

Powder Fineness (hereafter referred to as "reference D", downloaded from http://www.pharmacopeia.cn/v29240/usp29nf24s0_c811.html on Mar. 23, 2022) (Year: 2022).*

Aluminum carbonate (hereafter referred to as "reference A", NCBI (2022). PubChem Compound Summary for CID 10353966, Aluminum carbonate. Retrieved Mar. 23, 2022 from https://pubchem.ncbi.nlm.nih.gov/compound/Aluminum-carbonate, created on Oct. 25, 2006) (Year: 2006).*

Boric acid, aluminum salt (hereafter referred to as "reference B", NCBI (2022). PubChem Compound Summary for CID 16204948, Boric acid, aluminum salt. Retrieved Mar. 23, 2022 from https://pubchem.ncbi.nlm.nih.gov/compound/Boric-acid_-aluminum-salt, created Jul. 11, 2007) (Year: 2007).*

English language translation of Bzhasso ("New Catalysts for Maleic acid Hydration", Zhurnal Prikladnoi Khimii (Sankt-Peterburg, Russian Federation), 1969, 42(7), p. 1610-1614) (Year: 1969).*

Indian Examination Report issued for Indian Patent Application No. 201921028680, dated Feb. 25, 2021 in 6 pages.

International Search Report issued for International Patent Application No. PCT/IN2020/050608, dated Sep. 24, 2020 in 3 pages.

Japanese Office Action issued for Japanese Patent Application No. 2021-565840, dated Jul. 1, 2022 in 9 pages including English translation.

Extended European Search Report issued in the corresponding European Patent Application No. 20841483.9, dated Jul. 27, 2022 in 9 pages.

* cited by examiner

PRODUCTION OF MALIC ACID

CROSS-REFERENCE TO RELATED APPLICATIONS

This application is a continuation of International Application No. PCT/IN2020/050608 filed om Jul. 15, 2020, which claims priority to Indian Patent Application No. 201921028680 filed on July 16 and Indian Patent Application No. 202021009475 filed on Mar. 5, 2020. The entire disclosures of these applications are incorporated by reference herein.

TECHNICAL FIELD

The present subject matter relates generally to the production of malic acid, and in particular to the production of malic acid from different feedstock starting from butane, benzene, ortho-xylene, naphthalene or from intermediate products obtained by the processing of butane, benzene, ortho-xylene, naphthalene.

BACKGROUND

Malic acid is traditionally manufactured by the hydration of maleic acid, which is prepared by the dissolution of maleic anhydride in demineralized water, or using a mixture of maleic acid and fumaric acid under conditions of high pressure and high temperature. The time taken to attain equilibrium, i.e., formation of an equilibrium mixture of malic acid, fumaric acid, and trace amounts of unreacted maleic acid, which is considered as the time to reach completion of the reaction for a given quantity of maleic acid or its isomer fumaric acid or a mixture thereof, varies from 4 to 8 hours.

Catalysts have been found to increase the productivity of malic acid in the aqueous hydration of maleic acid. In a typical hydration reaction, maleic acid is hydrated in the presence of various catalysts, including sulfuric acid.

U.S. Pat. No. 3,379,756 describes a process for the synthesis of malic acid from maleic acid, fumaric acid, and mixtures thereof in an aqueous reaction mixture at elevated temperature and pressure, wherein the process is performed in a reactor zone whose surfaces that are exposed to the reaction mixture consist of at least one material from the group of titanium, zirconium, tantalum, and alloys containing at least one of the said material.

U.S. Pat. No. 5,210,295 discloses a process for the hydration of an acid selected from maleic acid, fumaric acid and others, where the high temperature reaction is done in the presence of sodium ions in specified molar ratios.

In European Patent No. EP0515345, there is a mention of "New Catalysts for Hydration of Maleic Acid" by N. A. Bzhasso and M. P. Pyatnitskii, Zhur. Priklandnoi Khim., Volume 42, no. 7, pages 1610-1614 (1969) which reports that the hydroxides of aluminum and chromium, when added to aqueous solutions of maleic acid, increase the conversion of maleic acid to malic acid. Equilibrium amounts of fumaric acid were also found in the hydration product. It is further stated that the published Russian patents by the said authors, viz. USSR Pat. Nos. 208706 and 218874, had disclosed the hydration of maleic acid to malic acid by dissolving maleic acid in water and adding aluminum hydroxide, chromium sulfate or aluminum chloride as catalysts for the reaction. The use of chlorides and sulfates of aluminum result in the formation of acids, i.e., hydrochloric acid and sulfuric acid, respectively. This leads to severe corrosion in the reactor vessel due to the contact of these acids with the metal surface, especially in the downstream of the reactor, which contaminates the products. Further, these ions, namely, chlorides and sulfates of aluminum are highly soluble and have to be removed by ion exchange or by other expensive methods. The use of chromium hydroxide results in the formation of poisonous chromium malate, in addition to imparting color to the mother liquor. The chromium malates get concentrated in the mother liquor over a period of time and can precipitate along with the product and contaminate the product.

U.S. Pat. No. 3,379,757 discloses a process for the manufacture of malic acid from aqueous solutions of maleic acid resulting from the vapor phase catalytic oxidation of an organic compound such as benzene comprising ageing the resulting maleic acid solution in the presence of air, filtering the aged solution and heating the filtrate in a closed system under super atmospheric pressure to convert the maleic acid to malic acid. This ageing process is carried out in a rubber lined steel tower.

However, the conventional methods of production of malic acid have several disadvantages. Very high temperatures and pressures are required for the reaction, it takes a long time for the reaction to reach equilibrium, the reaction products are corrosive and poisonous leading to corrosion of reactor vessels, and additional processes are required for removing contaminants from the products, leading to higher capital and operating costs. Accordingly, a need exists for alternative methods for the manufacture of malic acid.

SUMMARY

Disclosed herein is a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (a) obtaining a feed comprising the second intermediate product; and (b) causing the feed to undergo hydration reaction in a tubular reactor or a continuous stirred tank reactor to produce malic acid.

In some embodiments, the feed may be reacted in the presence of a catalyst. In some embodiments, the catalyst may be selected from a group consisting of aluminum metal, borate salt of aluminum, and carbonate salt of aluminum.

In some embodiments, the catalyst may have a concentration in a range of about 50 mg/L to about 500 mg/L with respect to the crude maleic anhydride or equivalent in the feed.

In some embodiments, the size of the catalyst particles may be in a range of about 10 micron to about 800 micron.

In some embodiments, the feed to catalyst ratio may be in a range of about 1:0.00005 to about 1:0.0005.

In some embodiments, the method disclosed here comprises obtaining a raw material selected from a group consisting of butane, benzene, o-xylene, naphthalene, and combinations thereof. In some embodiments, the raw material may be processed to obtain the first intermediate product.

In some embodiments, gas stripping the crude maleic anhydride may comprise one of: passing nitrogen through heated crude maleic anhydride under vacuum to substantially remove the impurities; or passing air through heated crude maleic anhydride to substantially remove the impurities. In some embodiments, the step of passing air through heated crude maleic anhydride to substantially remove the impurities may be performed in a column. In other embodiment, gas stripping the crude maleic anhydride may comprise passing carbon dioxide through heated crude maleic anhydride under vacuum to substantially remove the impurities. In some embodiments, the flow rate of the air can be about 0.5 $Nm^3/h$ to about 20 $Nm^3/h$, or 0.5 $Nm^3/h$ to about 10 $Nm^3/h$ or 1 $Nm^3/h$ to 5 $Nm^3/h$, such as 3 $Nm^3/h$. In some embodiments, temperature of the column may be about 70° C. to about 100° C., such as about 75° C. to about 95° C., or about 90° C.

In some embodiments, subjecting the mixture to crystallization may comprise: cooling the mixture to a temperature below about 30° C., below about 25° C., or below about 15° C., such as about 10 degrees, Celsius in a plurality of stages to obtain crystals of maleic acid; and filtering out the crystals of maleic acid as the treated intermediate product.

In some embodiments, obtaining a feed may comprise mixing the second intermediate product with one or more of water, maleic acid, maleic anhydride, and fumaric acid.

In some embodiments, causing the feed to undergo hydration reaction may comprise passing the feed in the tubular reactor at a Reynold's number from about 2900 to about 10000, and preferably from about 5000 to about 7000. In some embodiments, the feed may be reacted at a temperature in a range of about 135-195° C. and a pressure of about 11-15 bar for about 1 to 2 hours. In some embodiments, the tubular reactor may be operated in one of a batch, semi-continuous, or continuous mode.

In some embodiments, in the batch mode, a solution comprising the products may be drained out completely after completion of reaction.

In some embodiments, in the semi-continuous mode, a part of the solution comprising the products may be removed after a predetermined period of time and an equal quantity of feed may be fed into the tubular reactor.

In some embodiments, in the continuous mode, a part of the solution comprising the products may be continuously removed and simultaneously the same quantity of feed may be fed into the tubular reactor.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components where possible.

DETAILED DESCRIPTION

The present subject matter relates to the production of malic acid from different raw materials or feedstock and their mixtures in different modes of operation with and without the using catalysts.

Traditionally, malic acid is commercially produced using pure maleic anhydride obtained by the distillation of crude maleic anhydride, or from pure fumaric acid. The crude maleic anhydride or crude fumaric acid are obtained by vapor phase oxidation/gas phase oxidation of organic compounds such as butane, benzene, furan, furfural, and the like. The gaseous mixture of mainly maleic anhydride released from the outlet of the reactor is cooled in a condenser to obtain a solid material, which is known as crude maleic anhydride. This crude maleic anhydride is subjected to distillation to produce pure maleic anhydride. The uncondensed gases exiting the condenser are scrubbed in water to produce crude maleic acid, called as scrubber solution. This maleic acid scrubber solution is further subjected to dehydration and azeotropic distillation with o-xylene followed by vacuum distillation to produce pure maleic anhydride. The pure maleic anhydride is then used for the production of malic acid.

However, purification of maleic anhydride is very expensive, and using the pure form of maleic anhydride leads to a great increase in the cost of malic acid production. Furthermore, this also adds to the time required for the production of malic acid. Production of pure maleic anhydride also involves considerable loss of maleic anhydride during purification. The method of production of malic acid of the present disclosure overcomes the problems and disadvantages associated with conventional methods of production of malic acid. The present disclosure relates to a method of production of malic acid and co-production of fumaric acid from butane, benzene, o-xylene (raw material), or from any other intermediate products formed during the production of maleic anhydride or phthalic anhydride in an integrated production process. Crude products formed during production of maleic anhydride, phthalic anhydride, maleic acid, fumaric acid, and the other similar compounds, and uncondensed vent gases recovered by dissolving in water, generally called scrubber solution, can be used, in addition to using the pure forms of these products as the raw materials. In one example, for purification of intermediate products, any one or more of the following processes known to those skilled in the art can be followed: adsorption, absorption, spray drying techniques, falling film evaporation. The method of production of malic acid of the present disclosure includes a simple treatment of the raw materials, which eliminates the need for the less eco-friendly and more expensive dehydration and distillation steps traditionally used in the purification of raw materials or intermediates. The production can be done in continuous, semi-continuous, batch modes, or any combination thereof. In one embodiment, the reactor used is a tubular reactor operated in continuous, semi-continuous, or batch mode. The process of the present disclosure can be carried out in a tubular reactor of suitable design to prevent plugging and promote high rate of conversion by maintaining a turbulent flow with Reynold's number in the range of 5000 to 7000. In the process of the present disclosure, there is no back-mixing in solution flow in the tubular reactor. This enhances the rate of reaction to achieve faster equilibrium conditions. Consequently, in the process of the present disclosure, there is a substantial reduction in cost, energy and duration to achieve equilibrium (reaction hours) leading to increased productivity. In some embodiments, the flow in the reactor can have Reynold's number from about 2900 to about 10000, from about 3000 to about 9000, from about 4000 to about 8000, from about 5000 to about 8000, from about 5000 to about 7000, from about 5500 to about 7000, or from about 6500 to about 7000. In some embodiments, the Reynolds number may be, for example, at least 2500, 3000, 3500, 4000, 4500, 5000, 5500, 6000, 6500, 7000, 7500, 8000, 8500, 9000, 9500, 10000, or within a range defined by any two of the aforementioned Reynolds numbers.

In another embodiment, the reactor is a stirred tank reactor. The reaction is performed in the presence of aluminum borate catalyst, which leads to lesser time required to achieve equilibrium compared to conventional methods and thus increases productivity. Nevertheless, a catalyst is not necessary in many embodiments described herein.

Further, the method does not require pure raw materials, as required in conventional methods, thus reducing costs significantly. The method also reduces the amount of effluent to be treated during production of pure maleic anhydride or pure maleic or fumaric acids. The method also reduces the time for the reaction to 1-2 hours. The reduction in time reduces the energy consumed during operations and thus reduces operating costs. In some embodiments, impurities may be present at 0.1% w/w, 0.2% w/w, 0.3% w/w, 0.4% w/w, 0.5% w/w, 0.6% w/w, 0.7% w/w, 0.8% w/w, 0.9% w/w, 1% w/w, or more of the raw materials. In some embodiments, the impurity may be acetic acid, acrylic acid, or a combination thereof.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a continuous stirred tank reactor to produce malic acid.

In another embodiment, the present subject matter includes a method of production of malic acid, the method comprising: (a) obtaining a raw material selected from a group consisting of butane, benzene, o-xylene, naphthalene, and combinations thereof; (b) processing the raw material to obtain the first intermediate product; (c) treating the first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by gas stripping the crude maleic anhydride; and passing an aqueous solution of the treated intermediate product through a carbon column to substantially remove retained impurities to form the second intermediate product; (d) obtaining a feed comprising the second intermediate product; and (e) causing the feed to undergo hydration reaction in a tubular reactor or a continuous stirred tank reactor to produce malic acid.

In yet another embodiment, the present subject matter includes, a method of production of malic acid, the method comprising: (a) obtaining a raw material selected from a group consisting of butane, benzene, o-xylene, naphthalene, and combinations thereof; (b) processing the raw material to obtain the first intermediate product; (c) treating the first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (d) obtaining a feed comprising the second intermediate product; and (e) causing the feed to undergo hydration reaction in a tubular reactor or a continuous stirred tank reactor to produce malic acid.

In an embodiment, the present subject matter includes a method of production of malic acid, the method comprising: (a) obtaining a raw material selected from a group consisting of butane, benzene, o-xylene, naphthalene, and combinations thereof; (b) processing the raw material to obtain the first intermediate product; (c) treating the first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by gas stripping the crude maleic anhydride; and passing an aqueous solution of the treated intermediate product through a carbon column to substantially remove retained impurities to form the second intermediate product; (d) obtaining a feed comprising the second intermediate product; and (e) causing the feed to undergo hydration reaction in a tubular reactor or a continuous stirred tank reactor to produce malic acid.

In yet another embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride comprises passing nitrogen through heated crude maleic anhydride under vacuum to substantially remove the impurities; or passing air through heated crude maleic anhydride to substantially remove the impurities or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor to produce malic acid. Passing air through heated crude maleic anhydride to substantially remove the impurities may be performed in a column, wherein the flow rate of the air is from about 0.5 $Nm^3/h$ to about 20 $Nm^3/h$, preferably from about 0.5 $Nm^3/h$ to about 10 $Nm^3/h$. The temperature of the column may be from about 70° C. to about 100° C., such as about 75° C. to about 95° C., or about 90° C. In other embodiment, gas stripping the crude maleic anhydride may comprise passing carbon dioxide through heated crude maleic anhydride under vacuum to substantially remove the impurities.

In a further embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization comprises: cooling the mixture to a temperature below about 15 degrees Celsius in a plurality of stages to obtain crystals of maleic acid; and filtering out the crystals of maleic acid as the treated intermediate product; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor to produce malic acid. In another embodiment, the mixture may be cooled to a temperature below about 10 degrees Celsius in a plurality of stages to obtain crystals of maleic acid.

In one embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product comprises mixing the second intermediate product with one or more of water, maleic acid, maleic anhydride, and fumaric acid; and (c) causing the feed to undergo hydration reaction in a tubular reactor or a continuous stirred tank reactor to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor at a Reynold's number from about 2900 to about 10000 to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor at a Reynold's from about 5000 to about 7000 to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor in the presence of a catalyst at a Reynold's number from about 2900 to about 10000 to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor in the presence of a catalyst selected from a group consisting of aluminum metal, borate salt of aluminum, and carbonate salt of aluminum at a Reynold's number from about 2900 to about 10000 to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor in the presence of a catalyst selected from a group consisting of aluminum metal, borate salt of aluminum, and carbonate salt of aluminum at a Reynold's number from about 2900 to about 10000 to produce malic acid, wherein the catalyst has a concentration in a range of about 50 mg/L to about 500 mg/L with respect to the crude maleic anhydride or equivalent in the feed.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor in the presence of a catalyst to produce malic acid, wherein the average diameter of the catalyst particles is in a range of about 10 micron to about 800 micron.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor or a continuous stirred tank reactor in the presence of a catalyst to produce malic acid, wherein the feed to catalyst ratio is in a range of about 1:0.00005 to about 1:0.0005.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction at a temperature in a range of about 135-195° C. and a pressure of about 11-15 bar for about 1 to 2 hours in a tubular reactor or a continuous stirred tank reactor to produce malic acid.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor to produce malic acid, wherein the tubular reactor is operated in one of a batch, semi-continuous, or continuous mode.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor to produce malic acid, wherein the tubular reactor is operated in a batch mode, wherein a solution comprising the products is drained out completely after completion of reaction.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor to produce malic acid, wherein the tubular reactor is operated in a semi-continuous mode, wherein, a part of the solution comprising the products is removed after a predetermined period of time and an equal quantity of feed is fed into the tubular reactor.

In an embodiment, the present subject matter includes a method of production of malic acid, the method comprising: (a) treating a first intermediate product to form a second intermediate product, wherein the first intermediate product is selected from a group consisting of crude maleic anhydride, crude maleic acid, crude fumaric acid, vent gas scrubber solution obtained from a phthalic anhydride production process or a maleic anhydride production process, and combinations thereof, and wherein the treating comprises: substantially removing impurities from the first intermediate product to obtain a treated intermediate product by: (i) gas stripping the crude maleic anhydride; or (ii) subjecting a mixture comprising one or more of the crude maleic acid, the crude fumaric acid, and the vent gas scrubber solution obtained from a phthalic anhydride production process or a maleic anhydride production process to crystallization; and passing an aqueous solution of the treated intermediate product through a carbon column to substantially remove retained impurities to form the second intermediate product; (b) obtaining a feed comprising the second intermediate product; and (c) causing the feed to undergo hydration reaction in a tubular reactor to produce malic acid, wherein the tubular reactor is operated in a continuous mode, a part of the solution comprising the products is continuously removed and simultaneously the same quantity of feed is fed into the tubular reactor.

Aspects of the present disclosure are further described in conjunction with the appended figures. It should be noted that the description and figures merely illustrate the principles of the present subject matter. It will thus be appreciated that various arrangements that embody the principles of the present subject matter, although not explicitly described or shown herein, can be devised from the description and are included within its scope.

Figure 1:
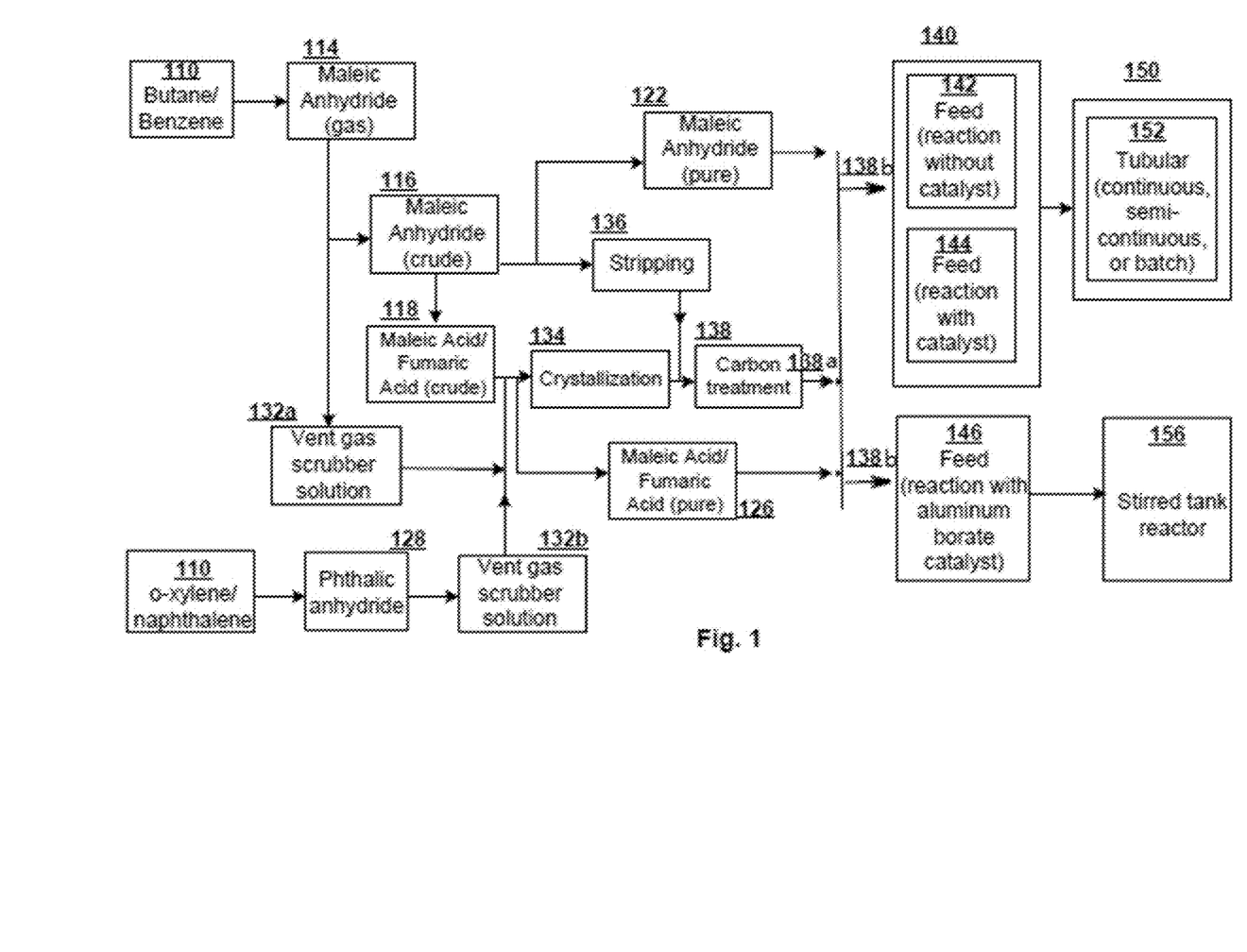
FIG. 1 illustrates a flow chart of the process of malic acid production, in accordance with an embodiment of the present disclosure.

FIG. 1 illustrates a flow chart of the process of malic acid production, in accordance with an embodiment of the present subject matter. 110 of FIG. 1 is the raw material; 116, 118, 132a, and 132b of the FIG. 1 are the first intermediate products; 122, 126, and 138a of FIG. 1 are the treated intermediate products and 138b of FIG. 1 is the second intermediate product of the present subject matter. In one embodiment, the starting raw material 110 is butane or benzene. In another embodiment, the starting raw material 110 is o-xylene or naphthalene. In one embodiment, butane or benzene is reacted with a catalyst in the vapor phase to produce maleic anhydride gas 114. The maleic anhydride gas 114 is condensed to produce crude maleic anhydride 116. The crude maleic anhydride 116 (first intermediate product) can be processed in multiple ways to form pure maleic anhydride 122 (treated intermediate product), or pure maleic acid or a mixture of pure maleic acid and pure fumaric acid 126 (treated intermediate product). The crude maleic anhydride 116 upon hydrolysis can produce crude maleic acid 118. The crude maleic acid 118 can isomerize and thus 118 can be a mixture of maleic acid and its isomer fumaric acid. The crude maleic acid or mixture of crude maleic acid and fumaric acid 118 can be purified to form pure maleic acid or a mixture of pure maleic acid and pure fumaric acid 126 by conventional processes. The crude maleic anhydride 116 can also be purified to form pure maleic anhydride 122 by conventional processes. Although conventional processes can be used to obtain pure maleic anhydride 122 or pure maleic acid or a mixture of pure maleic acid and pure fumaric acid 26 (treated intermediate product), the preferred treatment of crude maleic anhydride 116 and crude maleic acid 118 is gas stripping 136 and crystallization 134, respectively, followed by carbon treatment 138 in a carbon column to substantially remove retained impurities to form the second intermediate product 138b. Along with the crude maleic anhydride 116, uncondensed vent gases are produced. The uncondensed vent gases are passed through a scrubber to form a solution, herein referred to as vent gas scrubber solution 132a. The vent gas scrubber solution 132a comprises maleic anhydride, maleic acid, any unreacted raw material 110, and any other impurities.

In another embodiment, the raw material 110 is o-xylene or naphthalene. The raw material is reacted to produce phthalic anhydride 128. The product gases that are not condensed are passed through water to form another vent gas scrubber solution 132b, generally comprising any unreacted raw material 110, phthalic anhydride 128, and any other impurities.

In one embodiment, the crude maleic anhydride 116 can be subjected to a simple treatment before reaction. The maleic anhydride 116 can be subjected to gas stripping 136 and then a carbon treatment in a carbon column 138 to remove impurities. The gas stripping 136 can be performed in either nitrogen or air or carbon dioxide, with or without vacuum. In an example, the crude maleic anhydride 116 is heated and nitrogen is bubbled through. The temperature can be maintained at 80-85° C. Then, a vacuum is applied that allows impurities such as acetic acid and acrylic acid to be removed. The removal can be performed for about 5 hours. In another embodiment, the gas stripping 136 can be performed using air, at a temperature of about 90° C. for about 5 hours. In another example, the crude maleic anhydride 116 is heated and carbon dioxide is bubbled through. The temperature can be maintained at 80-85° C. Then, a vacuum is applied that allows impurities such as acetic acid and acrylic acid to be removed. The removal can be performed for about 5 hours. In another embodiment, the gas stripping 136 can be performed using air, at a temperature of about 90° C. for about 5 hours.

The treated crude maleic anhydride 116 can be dissolved in demineralized water and subjected to carbon treatment 138. The carbon treatment 138 can be performed by passing the dissolved maleic anhydride 116 through a carbon column to remove organic impurities that impart color, such as chromogens.

In another embodiment, the crude maleic acid or crude fumaric acid 118 and the vent gas scrubber solutions 132a and 132b can be subjected to controlled crystallization 134 to remove impurities. The crude maleic acid or fumaric acid 118 and vent gas scrubber solutions 132a and 132b can be slowly cooled to obtain crystals. A coolant, for example cold or chilled water at 5-10° C., can be used for cooling. The temperature of the solution can be carefully reduced from, for example 25° C. to 20° C. over 60 minutes and maintained for 60 additional minutes. Next, the temperature can be reduced to 15° C. over a duration of 90 minutes, then to 10° C. over a period of 120 minutes and the temperature is held there for about 120 minutes more. The maleic acid crystals thus obtained can be filtered, dried, and dissolved in water and subjected to the carbon treatment 138 to further remove impurities. The obtained maleic acid can contain less than 100 ppm of each of the impurities. This simple treatment of crystallization or stripping and then carbon treatment is less energy and labor intensive and hence cheaper compared to conventional purification techniques such as dehydration and distillation, which are widely followed.

The feed 140 for production of malic acid can be selected from the group consisting of crude maleic anhydride, pure maleic anhydride, crude maleic acid, crude fumaric acid, pure maleic acid, pure fumaric acid, vent gas scrubber solutions from the production of maleic anhydride from an organic compound such as butane, benzene, vent gas scrubber solutions from production of phthalic anhydride from an organic compound such as o-xylene or naphthalene, and any combination thereof. Water can be added to the raw materials described above, as required, to form a slurry or solution for passing through the reactors. The crude fumaric acid can be obtained from any of maleic anhydride, maleic acid, as a by-product of phthalic anhydride production, or by bio-technology routes known in the art.

In one embodiment, the feed 142 undergoes reaction in the absence of catalyst. In another embodiment, the feed 144 undergoes reaction in the presence of catalyst. The feed 140 undergoes reaction to produce a mixture of malic acid and fumaric acid at a temperature range of 135-195° C. and a suitable pressure. The reaction can be carried out either in the presence of a catalyst or without a catalyst. The catalyst is selected from aluminum metal or its borate or carbonate salts in its micronized form such that the use of the catalyst causes no corrosion in the inner surface of the reactor vessel, thus ensuring the catalytic process is corrosion free. In some specific embodiments, the catalyst is aluminum borate. The use of the alternative aluminum borate solution results in the formation of boric acid. Since boric acid is a weak acid, it does not corrode the reactors. Furthermore, using aluminum borate as the catalyst results in faster attainment of reaction equilibrium, compared to any other catalysts.

The presence and concentration of the catalyst when used in the reaction affects the process time, rate of reaction to attain equilibrium, and requirement of additional purification steps for removal of the catalyst used. However, in the catalytic process, the concentration of aluminum metal or aluminum borate or aluminum carbonate in its micronized form is in the range of 50-500 mg/L with respect to the crude maleic anhydride solution in the feed. In some embodiments, the concentration of catalyst can be, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, mg/L with respect to the crude maleic anhydride solution in the feed, or within a range defined by any two of the aforementioned concentrations. For example, the concentration of catalyst can be 50-100 mg/L, 60-100 mg/L, 70-100 mg/L, 50-500 mg/L, 100-200 mg/L, 300-500 mg/L, or 50-200 mg/L with respect to the crude maleic anhydride solution in the feed.

The micronized aluminum metal or its borate salt or carbonate salt in its powder or granular form has a particle size in the range of 10 micron to 800 micron. In some embodiments, the particle size of the catalyst can be 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, micron or within a range defined by any two of the aforementioned particle sizes. For example, in some embodiments, the particle size of the catalyst can be from about 10-50 micron, 10-100 micron, 10-200 micron, 50-200 micron, 100-500 micron, 100-300 micron, 300-800 micron, or 150-300 micron.

Preferably, the catalyst used is aluminum metal in its powder or granular form. The aluminum metal or its borate or carbonate salt solubilized in the feed solution 140 significantly speeds up the reaction to attain equilibrium. In one example, when using aluminum borate as the catalyst, the reaction attains equilibrium faster than when using any other catalysts. In one embodiment, the mass ratio of crude maleic acid to the catalyst is 1:0.0001 in the resulting solution. In some embodiments, the mass ratio of crude maleic acid to the catalyst can be 1:0.00005, 1:0.0001, 1:0.0002, 1:0.0003, 1:0.0004, 1:0.0005 or within a range defined by any two of the aforementioned ratios. For example, the ratio of crude maleic acid to the catalyst can be from 1:0.00005 to 1:0.0001, 1:0.0001 to 1:0.0002, 1:0.0002 to 1:0.0003, 1:0.0003 to 1:0004, 1:0004 to 1:0005, 1:0.0001 to 1:0.0005.

The feed 140 can be reacted in reactors 150. The reactor 150 can be a tubular reactor 152 that can be configured to operate in any of a continuous mode, semi-continuous mode, batch mode, or any combination thereof.

The tubular reactors 152 used for the production of malic acid from the feed solution are designed suitably to prevent plugging and promote high speed conversion, are made of a suitable material of construction including but not limited to titanium, tantalum, Hastelloy, Aluminum-Bronze or zirconium, with a high pressure circulating pump. The feed end of the tubular reactor 152 is connected to this pump, the other end is connected back to the suction of the pump for continuous circulation at pressure, with a bypass valve. Alternatively, there is a bypass in the piping after the tubular reactor 152 for removal of all or some material into a flash tank or a drain tank. This flash tank can also be connected back to the circulating pump suction. By circulation of the feed mixture or solution at high temperatures for a certain number of batches, then completely draining or partially draining and removing the stream, semi-continuous or continuous or batch processes for the production of malic acid and fumaric acid in flexible ratios as desired is achieved.

The tubular reactor can have an arrangement of tubes such as a loop reactor, circular, or spherical arrangement of tubes, which can enhance the rate of reaction and consequently reduce the processing hours to attain the production of malic acid in stoichiometric yield. The set of tubes in the tubular reactor are so arranged and interconnected and are provided with twisters and swirlers so as to provide a stream velocity of about 1.5 m/s, which leads to near full conversion of the feed material to the final equilibrium in reduced process time. In some embodiments, the stream velocity in the tubular reactor can be about 1.0, 1.1, 1.2, 1.3, 1.4, 1.5, 1.6, 1.7, 1.8, 1.9, or 2.0 m/s.

In some embodiments, the solution in the reactor may be heated to 135° C., 140° C., 145° C., 150° C., 155° C., 160° C., 165° C., 170° C., 175° C., 180° C., 185° C., 190° C., 195° C., or more, or within a range defined by any two of the aforementioned temperatures. For example, in some embodiments, the solution in the reactor may be heated to 135-195° C., 145-195° C., 135-150° C., 135-180° C., 150-195° C., or 145-185° C.

In some embodiments, the solution in the reactor may pressurized at 5, 5.5, 6, 6.5, 7, 7.5, 8, 8.5, 9, 9.5, 10, 10.5, 11, 11.5, 12, 12.5, 13, 13.5, 14.0, 14.5, 15.0, or more, or within a range defined by any two of the aforementioned pressures. For example, in some embodiments, the solution in the reactor may be pressurized from 5-15 bar, 5-10 bar, 10-15 bar, 11-15 bar, or 12-15 bar.

In some embodiments, the solution in the reactor may be subjected to heat and/or pressure for 10 min, 20 min, 30 min, 40 min, 50 min, 1 h, 1.5 h, 2.0 h, 2.5 h, 3.0 h, or more, or within a range defined by any two of the aforementioned times. For example, in some embodiments, the solution in the reactor may be subjected to heat and/or pressure for 30 min-2 h, 1-2 h, 1.5-2 h, or 1-3 h.

In an embodiment, the crude feed solution is pumped in to the tubular reactor assembly at high velocity. The solution is continuously circulated in the reactor. This solution is heated to a temperature of 135-195° C. at a pressure of 11-15 bar for about 1-2 hours. In another embodiment, when the process is conducted in the presence of catalyst, aluminum metal or its borate or carbonate salt solution is added to the crude feed solution, prior to pumping in to the tubular reactor, so that the mass ratio of crude feed solution to the catalyst is 1:0.0001 (100 ppm of catalyst) in the resulting solution.

In some embodiments, the malic acid production process can be carried out in any one of a batch process, semi-continuous process, or a continuous process. In the batch process, after the above operations, the solution is completely drained into a collection tank and taken for further processing. In the semi-continuous process, after the above operations, a part of the solution is drained after a fixed period of time and an equal quantity of feed solution containing the catalyst is fed into the tube, recirculated and again after a fixed period of time another fixed quantity is drained, and the process is repeated. In the continuous process, after the above operations, a very small quantity of the solution is drained into a flash tank continuously and simultaneously the same quantity of feed solution containing the catalyst is fed into the tubes.

The reaction products obtained are a mixture of fumaric acid and malic acid. The two acids are separated from the mixture by filtration or other conventional means. The volatile impurities and the color-causing compounds originating from crude maleic anhydride 116 and the scrubber solution 132a are removed by conventional purification processes. The mother liquor containing malic acid is concentrated to recover malic acid, which is further purified. The purification of the resulting malic acid can be carried out by a variety of means, including but not limited to, the use of ion exchangers, activated carbon in powder form, or passing malic acid through a series of carbon columns.

The boric acid formed when aluminum borate is used as a catalyst is removed from the mixture by processes known in the art.

The process of the present disclosure is carried out in a tubular reactor of suitable design to prevent plugging, promote high rate of conversion by maintaining a turbulent flow with Reynold's number in the range of 5000 to 7000. The turbulence in the tubular reactor is achieved and maintained by the optimal selection of the following parameters that affect the solution flow rate: diameter (size) of reactor and velocity. In the process of the present disclosure, there is no back-mixing in solution flow in the tubular reactor. This enhances the rate of reaction to achieve faster equilibrium conditions. Consequently, in the process of the present disclosure, there is a substantial reduction in costs, energy and reduced duration to achieve equilibrium (reaction hours) leading to increased productivity.

In one example, with turbulence in the tubular reactors 152, the Reynolds number is 6700, calculated using known method using the flow rate and the dimensions of the reactor. In another example, when there is no turbulence in the tubular reactors 152, the Reynolds number is calculated to be 2400. In the process of the present disclosure, there is no back-mixing in solution flow in the tubular reactor. This enhances the rate of reaction to achieve faster equilibrium conditions. Consequently, in the process of the present disclosure, there is a substantial reduction in costs, energy and duration to achieve equilibrium (reaction hours) leading to increased productivity.

In another embodiment, reaction is carried out in the presence of aluminum borate catalyst in feed 146 in a stirred tank reactor 156. Any of the feed compositions described before can be used. For example, the feed 146 for production of malic acid in a stirred tank reactor 156 can be selected from the group consisting of crude maleic anhydride, pure maleic anhydride, crude maleic acid, crude fumaric acid, pure maleic acid, pure fumaric acid, vent gas scrubber solutions from the production of maleic anhydride from butane, benzene, vent gas scrubber solutions from production of phthalic anhydride from o-xylene or naphthalene, and any combinations thereof. The use of the catalyst can decrease reaction time by up to 3 times compared to conventional methods. This increases the efficiency of the operation process, reducing costs, and improving productivity.

Figure 2:
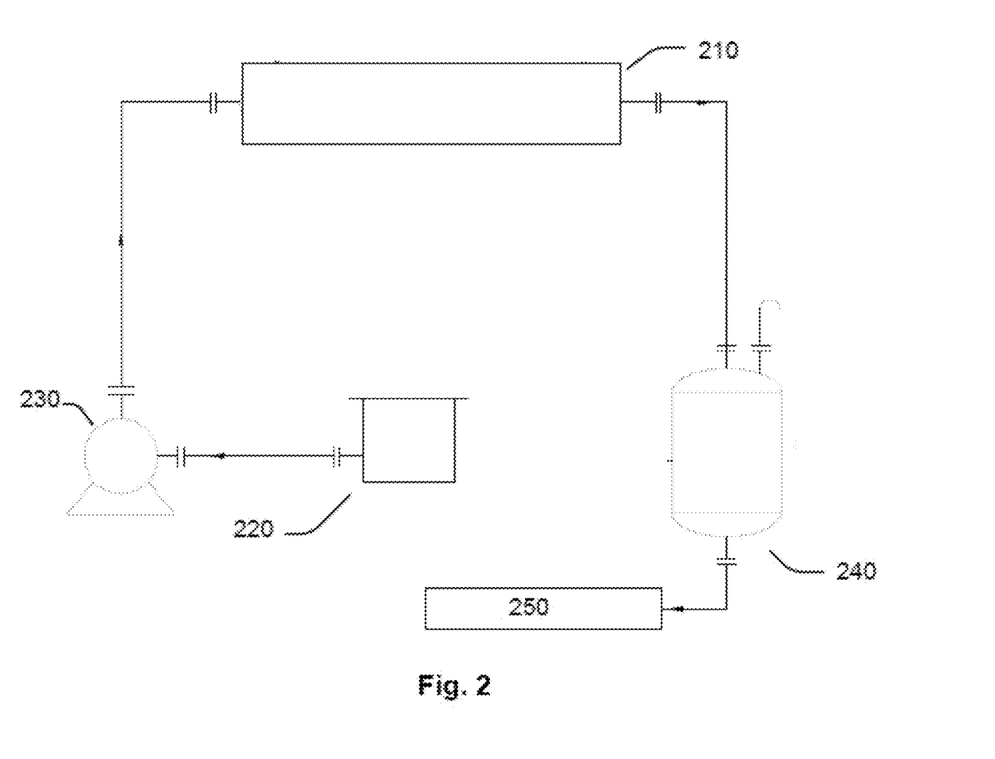
FIG. 2 is a schematic illustration of a continuous tubular reactor system for production of malic acid, in accordance with an embodiment of the present disclosure.

FIG. 2 is a schematic illustration of a continuous tubular reactor system for production of malic acid, in accordance with an embodiment of the present subject matter. The reactor system comprises of a tubular reactor 210. Feed from a feed tank 220 is fed to the tubular reactor 210 via a circulation pump 230. The reaction for formation of malic acid occurs in the tubular reactor 210. The tubular reactor 210 is designed such that the feed has a large enough residence time for the reaction to attain equilibrium and feed is not recirculated back through the tubular reactor 210. The solution-slurry with the reaction products is drained into a flash tank 240 and the products 250 from the flash tank 240 can be sent for further processing such as purification and the like.

Figure 3:
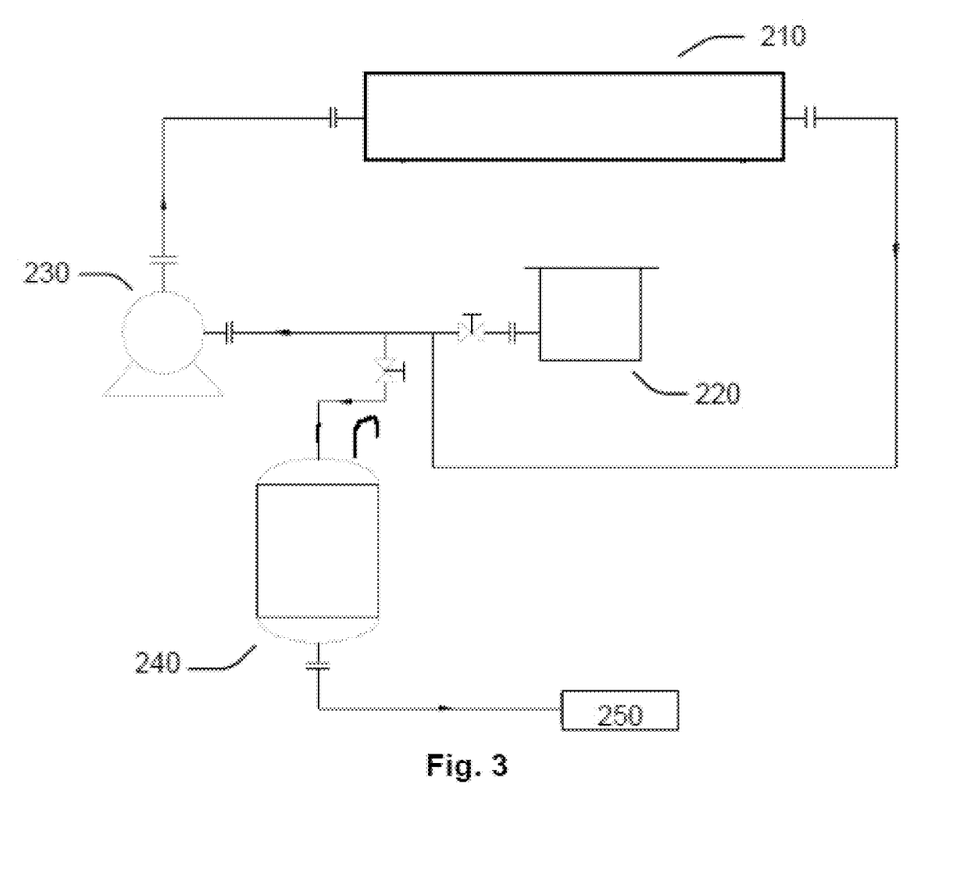
FIG. 3 is a schematic illustration of a semi-continuous tubular reactor system for production of malic acid, in accordance with an embodiment of the present disclosure.

FIG. 3 is a schematic illustration of a semi-continuous tubular reactor system for production of malic acid, in accordance with an embodiment of the present subject matter. Feed from the feed tank 220 is fed into the tubular reactor 210 via circulation pump 230. During processing, a part of the product stream is drained into the flash tank 240 and a part is recirculated back to the tubular reactor 210 via the circulation pump 230, forming a semi-continuous process. The recirculation of part of the product stream can be done several times until the desired conversion to products 250 is achieved.

In another embodiment, the reactor system comprises a number of such tubular reactor sub-systems, each system with a pump, flash tanks and recirculation piping, with each sub-system connected in series, leading to stepwise increase in conversion of each sub-system, and eventually once the overall residence-conversion time is ensured to final equilibrium conversion, the resultant final outflow from the overall system is drained to undergo further separation and purification processes.

Figure 4:
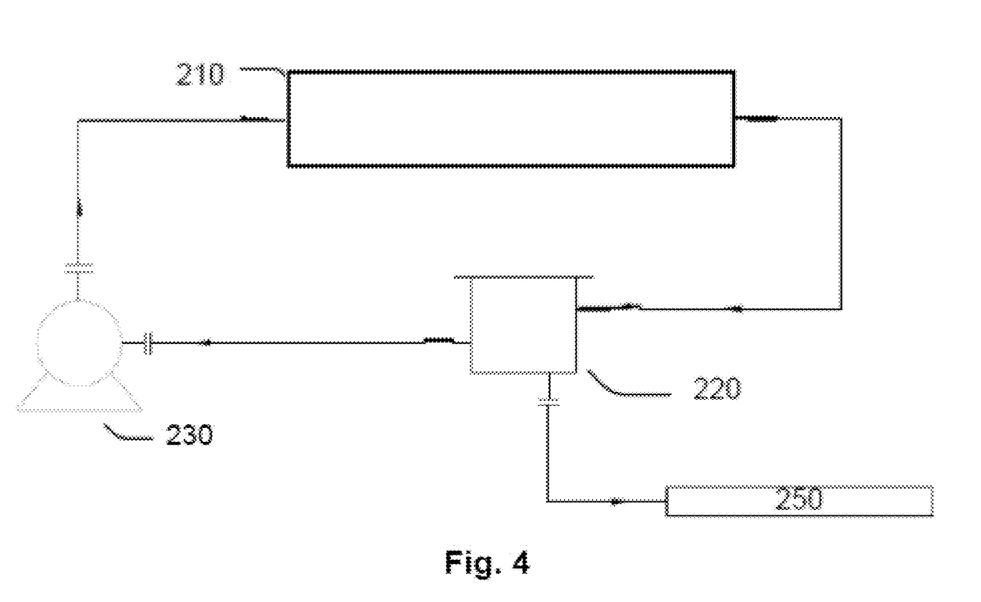
FIG. 4 is a schematic illustration of a batch tubular reactor system for production of malic acid, in accordance with an embodiment of the present disclosure.

FIG. 4 is a schematic illustration of a batch tubular reactor system for production of malic acid, in accordance with an embodiment of the present subject matter. The tubular reactor 210 is part of a closed circulation system, wherein the feed is circulated for a sufficient number of cycles until near complete conversion of the reactants is obtained. After completion of the reaction, the process is stopped, and the products 250 are drained to undergo further separation and purification.

Figure 5:
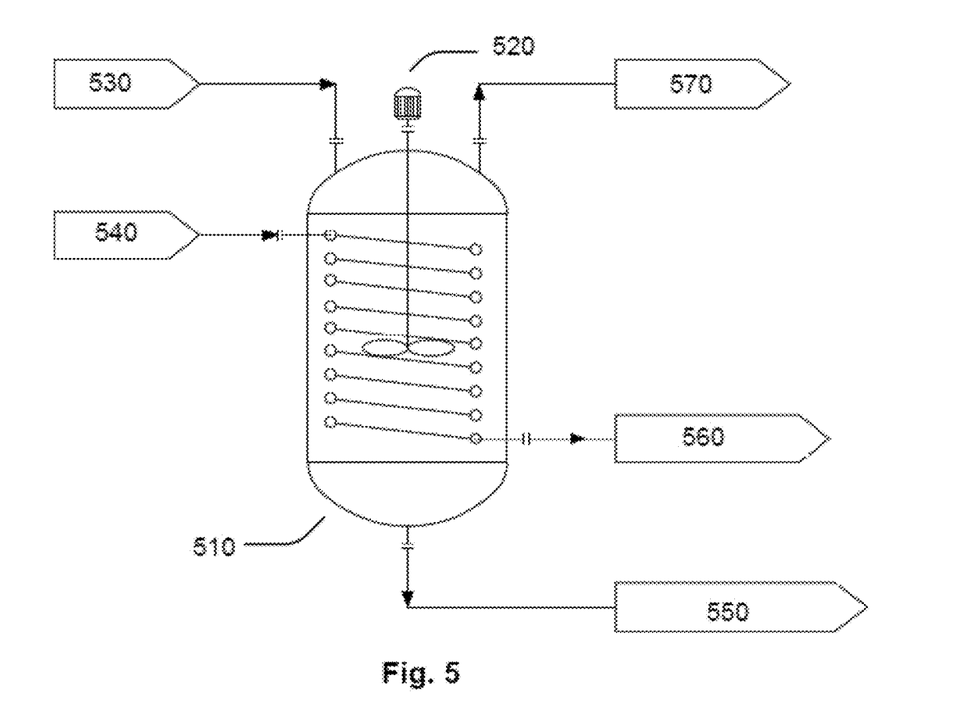
FIG. 5 is a schematic illustration of a stirred tank reactor for production of malic acid, in accordance with an embodiment of the present disclosure.

FIG. 5 is a schematic illustration of a stirred tank reactor for production of malic acid, in accordance with an embodiment of the present subject matter. The reactor system comprises a tank 510 comprising a stirrer 520. Feed is added to the tank 510 via a feed inlet 530 and steam is fed into the tank 510 via a steam inlet 540. The feed is continuously stirred in the tank 510 by the stirrer 520 for the desired period of time to ensure near complete conversion of the reactants into products. The products are removed via outlet 550, any condensate is removed via condensate outlet 560, and gases are removed via vapor outlet 570. The feed can be any of the raw materials described before, or any combination thereof. The reaction is performed in the presence of aluminum borate catalyst. The presence of the catalyst reduces the reaction time by about three times compared to conventional methods, thus improving productivity.

EXAMPLES

The disclosure will now be illustrated with working examples, which are intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

The examples show feedstocks 1, 2, and 3. However, any combinations thereof can also be used.

Mode 1 A: Tubular Batch, Semi-continuous and Continuous Process with Catalyst

Using Aluminum Borate as Catalyst
  Experimental Details:
  Maleic Acid solution: 17 liters (or) Fumaric Acid Solution: 17 liters
  Concentration of Maleic Acid solution in water: 45% w/v
  Reaction Temperature: 185° C.
  Reactor Pressure: 12 bar.
  Feedstock Details:
  Three different feedstock compositions below in Table 1:

TABLE 1

Different feedstock compositions

Feedstock 1-Pure Maleic acid + Water/Pure Fumaric acid + Water/ Mixture of these in any proportion or combination – feedstock can be derived from n-Butane/Benzene.
Feedstock 2-Crude Maleic acid + Water/Crude Fumaric acid + Water/ Mixture of these in any proportion or combination – feedstock can be derived from n-Butane/Benzene.
Feedstock 3-Maleic Acid Scrubber Solution + Crude Fumaric acid + Water/Mixture of these in any proportion or combination – feedstock can be derived from o-Xylene/Naphthalene/Butane The feedstock in these experiments can be defined as any one of the following:
  1. 6.46 kg of maleic anhydride dissolved in 13.12 liter of demineralized water so that the quantity of maleic acid is 7.65 kg.
  2. 7.65 kg of pure fumaric acid.
  3. A mixture of items 1 and 2 in any proportion or combination in that the quantity of such mixture is equivalent to 7.65 kg of maleic acid.

Experimental Procedure:

The feedstock was dissolved in 13.12 liter of demineralized water in a feed tank. To this vessel, an aluminum-based catalyst was added and stirred well so that the final solution contained 100 mg/L (ppm) of aluminum borate or aluminum powder catalyst with respect to the feed taken. The ratio of raw material to catalyst was 1:0.0001. If necessary, some heating was given to dissolve the catalyst. The solution was charged into a tubular reactor and thoroughly circulated.

The temperature of the solution in the reactor was gradually increased to 135-195° C. and the pressure in the reactor reached about 12 bar. This condition was maintained as the solution was continuously circulated in the reactor for completion of reaction.

In the case of a batch process, after completion of reaction, the heating was cut off. The reactor system was depressurized carefully by controlled venting of steam. As the temperature of the reactor reached approximately 80-90° C., the whole liquid slurry mass from the reactor vessel was drained completely into a separate vessel. The solution was cooled to ambient temperature.

Fumaric acid was separated and the mother liquor containing malic acid, some fumaric acid in solution and a small percentage of unreacted maleic acid was taken for further stages of separation and purification.

In the semi-continuous process, after completion of the reaction, 1000 mL of the solution was drained into the flash tank, the reactor pressure reduced to around 10 bar, the same quantity of feed maleic acid solution was fed into the titanium tube assembly, and the reaction was carried out for another 20 minutes and then the 1000 mL solution was drained into the flash tank. This process was continued for several hours to be termed as a semi continuous process. The whole liquid slurry mass from the reactor vessel was drained completely into a separate vessel. The solution was cooled to ambient temperature. After this, the process followed the same steps as a batch process.

In the continuous process, after completion of reaction duration the solution in the reactor was drained into the flash tank at the rate of 50 mL/min Simultaneously, an equal quantity of feed maleic acid solution was fed into the titanium tube. This process was continued for several hours, the whole liquid slurry mass from the reactor vessel was drained completely into a separate vessel. The solution was then cooled to ambient temperature. After this, the process followed the same steps as a batch process.

The same experiments were carried out using aluminum hydroxide and aluminum carbonate catalyst instead of aluminum borate. The results of these experiments are shown in Table 2.

Mode 1 B: Tubular Batch, Semi-continuous and Continuous Process without Catalyst The same processes were carried out without the usage of catalyst in all three modes of operation: Tubular Batch, Tubular Semi-continuous and Tubular Continuous.

Turbulence Regimes

The time taken for attaining the equilibrium depended on the turbulence achieved and given below are the two regimes of operation characterized by turbulence:
  1) With turbulence, Reynolds number equals 6,700 (calculated by known methods).
  2) Without turbulence, Reynolds number equals 2,400 (calculated by known methods)

Mode 2 A: Stirred Tank Reactor—Batch Process with Catalyst

Using Aluminum Borate as Catalyst
Experimental Details
Maleic Acid solution: 50 liter (or) Fumaric Acid Solution: 50 liter
Concentration of Maleic Acid solution in water: 45% w/v
Catalyst (Aluminum Borate)—100 mg/liter with respect to Maleic acid (100 ppm)
Reaction Temperature: 185° C.
Reactor Pressure: 12 bar.
Reaction Duration: 120 minutes
Feedstock compositions are the same as those used in tubular reactor processes.
Feedstock Details:
The feedstock used in these experiments is defined as any one of the following:
1. 21.12 kg maleic anhydride dissolved in 43 liters of demineralized water so that the quantity of maleic acid is 25 kg.
2. 25 kg of fumaric acid.
3. A mixture of items 1 and 2 in any proportion or combination in that the quantity of such mixture is equivalent to 25 kg of maleic acid.
4. Catalyst concentration: 100 ppm of aluminum-based catalyst.

Experimental Procedure:

21.12 kg of maleic anhydride (or 25 kg of fumaric acid) was dissolved in 43 liter of demineralized water in a separate vessel. To this pure aluminum borate was added and stirred well so that the final solution contained 100 mg/liter of aluminum borate with respect to the amount of maleic acid (i.e. maleic acid:aluminum borate in the ratio of 1:0.0001 by weight). If necessary, some heating was provided to dissolve the aluminum borate. This solution was charged into the Stirred Vessel Reactor and thoroughly agitated. The temperature of the solution in the closed reactor was slowly increased to 135-195° C. and the pressure in the reactor goes up to around 12 bar while agitation was continued. This condition is maintained as the solution is in the reactor for completion of reaction. After completion of reaction, the heating was cut off. The reactor was depressurized carefully by controlled venting of steam. Cooling water circulation may be given through the jacket of the reactor to reduce the temperature of the solution to 80-90° C. The whole liquid slurry mass from the reactor vessel was drained completely, into a separate vessel. The solution was cooled there to ambient temperature in about 6-8 hours. From here on, the process follows the same steps as the other tubular reactor processes explained above.

The same experiments were carried out using aluminum hydroxide and aluminum carbonate catalyst instead of aluminum borate. The results are shown in Table 2.

Mode 2 B: Stirred Tank Reactor Batch Process—Without Catalyst

The same experiment as above was carried out in the stirred tank reactor without using catalyst. The results are included in the consolidated table (Table 2).

Given below is the consolidated table (Table 2) containing the different feedstock compositions, modes of operation, turbulence, and presence/absence of catalyst and the time taken to achieve equilibrium (reaction duration) for different combinations of these parameters.

TABLE 2

Different feedstock compositions, modes of operation, turbulence, and presence/absence of catalyst and the time taken to achieve equilibrium (reaction duration) for different combinations of these parameters.

| S. No | Feedstock Used | Modes of Operation | Turbulence | Catalyst | Reaction duration | Reynold's Number |
|---|---|---|---|---|---|---|
| Mode - 1 A & 1 B ||||||| 
| 1 | Feedstock 1, 2, 3 | Tubular batch, Semi-Continuous, Continuous | Yes | No | 90 minutes | 6000 to 7000 |
| 2 | Feedstock 1, 2, 3 | Tubular batch, Semi-Continuous, Continuous | No | No | 200 minutes | 2000 to 2500 |
| 3 | Feedstock 1, 2, 3 | Tubular batch, Semi-Continuous, Continuous | Yes | 100 ppm of Aluminum borate | 60 minutes | 6000 to 7000 |
| 4 | Feedstock 1, 2, 3 | Tubular batch, Semi-Continuous, Continuous | No | 100 ppm Aluminum borate | 100 minutes | 2000 to 2500 |
| 5 | Feedstock 1, 2, 3 | Tubular batch, Semi-Continuous, Continuous | Yes | 100 ppm Aluminum Hydroxide or Aluminum Powder | 75 minutes | 6000 to 7000 |
| 6 | Feedstock 1, 2, 3 | Tubular batch, Semi-Continuous, Continuous | No | 100 ppm Aluminum Hydroxide or Aluminum Powder | 115 minutes | 2000 to 2500 |
| Mode - 2 A & 2 B minutes |||||||
| 7 | Feedstock 1, 2, 3 | Stirred Tank Reactor Batch | No | 100 ppm Aluminum borate | 120 minutes | N/A |
| 8 | Feedstock 1, 2, 3 | Stirred Tank Reactor | No | No | 360 minutes | N/A |
| 9 | Feedstock 1, 2, 3 | Stirred Tank Reactor Batch | No | 100 ppm Aluminum Hydroxide (or) Aluminum Carbonate | 150 minutes | N/A |

As shown in Table 2, the use of turbulence alone, catalyst alone, or a combination of turbulence and catalyst reduced the reaction time required to attain equilibrium in the batch, semi-continuous, or continuous modes in a tubular reactor. Use of aluminum borate as a catalyst along with turbulence shows the least time required for attaining equilibrium. For the stirred tank reactor, using aluminum borate as the catalyst showed the smallest reaction time to attain equilibrium compared to using no catalyst or using aluminum hydroxide as catalyst.

The exact quantities of malic acid, fumaric acid and unreacted maleic acid in all these processes were measured from the quantities obtained and the stoichiometric conversion was calculated.

Stoichiometric conversion (Table 3) of feedstock obtained from all these processes as described above are shown in the table below. These are nearly the same as that obtained in any batch process, assuming that the total acid quantity before the reaction is 100% maleic acid or 100% fumaric acid or 100% malic acid expressed as maleic acid.

TABLE 3

Obtained stoichiometric conversion of feedstock.

| S. No | Name of the Compound | Stoichiometric Conversion of Feedstock |
|---|---|---|
| 1. | Malic Acid | 57 to 58% |
| 2. | Fumaric Acid | 37 to 38% |
| 3. | Maleic Acid | 1.2 to 1.5% |
| 4. | Loss/Unaccounted ($CO$, $CO_2$ etc.) | 2 to 3% |

Thus, as shown in Table 3, the stoichiometric conversion of feedstock is comparable to any other batch process. However, the time required to attain equilibrium was reduced significantly, as explained before, thus increasing productivity.

Example: Maleic Acid and Vent Gas Scrubber Treatment

The treatment process can be performed for any or all of the crude maleic acid or fumaric acid 118 or the vent gas scrubber solution from the manufacture of maleic anhydride after partial condensation of gaseous maleic anhydride 132a, or vent gas scrubber solution from the manufacture of phthalic anhydride 132b after condensation of gaseous phthalic anhydride and separation 132b. One liter of maleic acid scrubber solution containing about 46% w/v of maleic acid, about 0.7% of acetic and about 0.4% of acrylic acid was taken in a glass beaker. This beaker was provided with a stirrer and the speed was maintained at 25 rpm. Chilled or cold water was circulated through the jacketed arrangement in the beaker. The contents of the beaker were at room temperature (about 25° C.).

The temperature was gradually reduced to 20° C. over a period of 60 minutes. This temperature was then maintained for another 60 minutes. Some crystallisation may be observed. By adjusting the cooling water flow, the temperature was reduced further to 15° C. over a period of 90 minutes. Likewise, the temperature of maleic acid solution was reduced even further to 10° C. over a period of 2 hours. This temperature was maintained for 120 minutes.

The crystallisation was carefully controlled in this manner. The maleic acid crystals so obtained were filtered and dried and subjected to further treatment for colour removal by carbon treatment. The mother liquor was recycled. Impurity analysis of maleic acid crystals in dry basis is provided in Table 4.

TABLE 4

Impurities concentration before and after treatment

| S. No | Impurity | Before Treatment | After Treatment |
|---|---|---|---|
| 1 | Acetic Acid (Impurity) | 0.7% (approx.) | Less than 0.01% |
| 2 | Acrylic Acid (Impurity) | 0.3%-0.4% (approx.) | Less than 0.01% |

Table 4 indicates that after the crystallization and passing over carbon column, the impurities in the crude maleic acid solution is less than 0.01%.

Example: Crude Maleic Anhydride Treatment

One kg of crude maleic anhydride was taken in a 2.0 liter, 3-necked round-bottomed flask. The crude maleic anhydride typically about 0.1% of acetic acid and 0.1% of acrylic acid as impurities. The flask was provided with a stirrer and speed of rotation was maintained at 100 along with nitrogen bubbling and vacuum arrangements. This flask was heated through a heating mantle and the temperature of the flask was maintained at an optimal range of 80 to 85° C. Once the temperature was within the range, a vacuum of 20 torr was created with suitable arrangements and under inert atmosphere. The temperature was maintained under these conditions for over a period of 3 hours.

The two major impurities namely acetic acid and acrylic acid were almost completely stripped out from crude maleic anhydride such that the quality of treated maleic anhydride was as shown Table 5. This maleic anhydride was further subjected to color removal by carbon treatment.

TABLE 5

Impurity analysis of crude maleic anhydride before and after treatment

| S. No | Impurity | Before Treatment | After Treatment |
|---|---|---|---|
| 1 | Acetic Acid (Impurity) | 0.1% (by weight) | Less than 0.01% |
| 2 | Acrylic Acid (Impurity) | 0.1% (by weight) | Less than 0.01% |

Table 5 shows that after treatment of maleic anhydride, the impurities were reduced to less than 0.01%.

Example: Crude Maleic Anhydride Treatment

About 25 kg of crude maleic anhydride was taken in a 35 liter-capacity stainless steel feed tank with a jacketed arrangement. Heating was provided through low-pressure steam. The feed typically contained about 0.1% of acetic acid and 0.1% of acrylic acid as impurities.

The feed tank discharge outlet was connected to a stainless-steel column of about 3-meter height and 50 mm diameter and filled with structural packing material. The adjusted flow rate of crude maleic anhydride was about 5 kg/h at an operating temperature of 90° C. Air flow rate from the bottom was about 3 $Nm^3$/h. The temperature of the column was maintained at about 90° C. for over a continuous period of 5 hours.

The treatment can be described as a continuous countercurrent operation of stripping by air for removal of impurities namely acetic acid and acrylic acid in crude maleic anhydride. The two major impurities namely acetic acid and acrylic acid were almost completely stripped out from crude maleic anhydride such that the quality of treated maleic anhydride was as per the Table 6.

TABLE 6

Impurity analysis of crude maleic anhydride before and after treatment

| S. No | Impurity | Before Treatment | After Treatment |
|---|---|---|---|
| 1 | Acetic Acid (Impurity) | 0.1% (by weight) | Less than 0.01% |
| 2 | Acrylic Acid (Impurity) | 0.1% (by weight) | Less than 0.01% |

The treated crude maleic anhydride was dissolved in demineralized water to make crude maleic acid solution. This maleic anhydride was further subjected to colour removal by carbon treatment.

Although embodiments for production of malic acid are described in language specific to structural features, it is to be understood that the specific features and methods are disclosed as example embodiments for implementing the claimed subject matter.

What is claimed is:

1. A method of production of malic acid, the method comprising:
   (a) treating a first intermediate product to form a second intermediate product, wherein the first intermediate product is selected from the group consisting of crude maleic acid, crude fumaric acid, a vent gas scrubber solution obtained from a phthalic anhydride production process, a vent gas scrubber solution obtained from a maleic anhydride production process, and combinations thereof, and wherein the treating comprises:
      removing impurities from the first intermediate product to obtain a treated intermediate product by:
         subjecting a mixture comprising one or more of the crude maleic acid, the crude fumaric acid, the vent gas scrubber solution obtained from a phthalic anhydride production process and the vent gas scrubber solution obtained from a maleic anhydride production process to crystallization comprising cooling the mixture to a temperature below about 30° C.; and
         passing an aqueous solution of the treated intermediate product through a carbon column to remove retained impurities to form the second intermediate product;
   (b) obtaining a feed comprising the second intermediate product; and
   (c) causing the feed to undergo a hydration reaction in a tubular reactor or a continuous stirred tank reactor to produce malic acid,
   wherein the hydration reaction of the feed is carried out in the presence of a catalyst selected from the group consisting of a borate salt of aluminum and a carbonate salt of aluminum.

2. The method of claim 1, wherein the catalyst is in the form of particles having an average diameter in a range of about 10 micron to about 800 micron.

3. The method of claim 1, wherein the feed to the catalyst weight ratio is in a range of about 1:0.00005 to about 1:0.0005.

4. The method of claim 1, wherein the first intermediate product is a product of processing a raw material selected from the group consisting of butane, benzene, o-xylene, naphthalene, and combinations thereof.

5. The method of claim 1, wherein subjecting the mixture to crystallization comprises:
   cooling the mixture to a temperature below about 15 degrees Celsius in a plurality of stages to obtain crystals of maleic acid; and
   filtering out the crystals of maleic acid as the treated intermediate product.

6. The method of claim 1, wherein obtaining a feed comprises mixing the second intermediate product with one or more of water, maleic acid, maleic anhydride, and fumaric acid.

7. The method of claim 1, wherein causing the feed to undergo the hydration reaction comprises passing the feed in the tubular reactor at a Reynolds number from about 2900 to about 10000.

8. The method of claim 1, wherein the feed is reacted at a temperature in a range of about 135-195° C. and a pressure of about 11-15 bar for about 1 to 2 hours.

9. The method of claim 1, wherein the tubular reactor is operated in one of a batch, semi-continuous, or continuous mode.

10. The method of claim 9, wherein, in the batch mode, a solution comprising the products is drained out completely after completion of reaction.

11. The method of claim 9, wherein, in the semi-continuous mode, a part of the solution comprising the products is removed after a predetermined period of time and an equal quantity of feed is fed into the tubular reactor.

12. The method of claim 9, wherein, in the continuous mode, a part of the solution comprising the products is continuously removed and simultaneously the same quantity of feed is fed into the tubular reactor.

13. The method of claim 1, wherein the catalyst is aluminum borate.

14. A method of production of malic acid, the method comprising:
   (a) treating a first intermediate product to form a second intermediate product, wherein the first intermediate product is crude maleic anhydride, and wherein the treating comprises:
      removing impurities from the first intermediate product to obtain a treated intermediate product by:
         gas stripping the crude maleic anhydride; and
         passing an aqueous solution of the treated intermediate product through a carbon column to remove retained impurities to form the second intermediate product;
   (b) obtaining a feed comprising the second intermediate product; and
   (c) causing the feed to undergo a hydration reaction in a tubular reactor or a continuous stirred tank reactor to produce malic acid,
   wherein the hydration reaction of the feed is carried out in the presence of a catalyst selected from the group consisting of a borate salt of aluminum, and a carbonate salt of aluminum.

15. The method of claim 14, wherein gas stripping the crude maleic anhydride comprises one of:
   passing nitrogen through heated crude maleic anhydride under vacuum to remove the impurities; or
   passing air or carbon dioxide through heated crude maleic anhydride to remove the impurities.

16. The method of claim 15, wherein passing air through heated crude maleic anhydride to remove the impurities is performed in a column.

17. The method of claim 16, wherein the flow rate of the air is from about 0.5 $Nm^3/h$ to about 20 $Nm^3/h$.

18. The method of claim 16, wherein the temperature of the column is from about 70° C. to about 100° C.

* * * * *